United States Patent [19]
Melendez et al.

[11] Patent Number: 6,097,479
[45] Date of Patent: Aug. 1, 2000

[54] CRITICAL ANGLE SENSOR

[75] Inventors: Jose L. Melendez, Plano; Richard A. Carr, Rowlett; Dwight U. Bartholomew, Dallas, all of Tex.

[73] Assignee: Texas Instruments Incorporated, Dallas, Tex.

[21] Appl. No.: 08/942,159

[22] Filed: Oct. 1, 1997

[51] Int. Cl.[7] .................................................. G01N 21/41
[52] U.S. Cl. ............................................................ 356/136
[58] Field of Search .............................................. 356/136

[56] References Cited

U.S. PATENT DOCUMENTS

| | | | |
|---|---|---|---|
| 4,749,274 | 6/1988 | Aoki et al. | 356/136 |
| 4,834,104 | 5/1989 | Kreinick et al. | 356/136 |
| 4,895,444 | 1/1990 | Miyata et al. | 356/136 |
| 4,912,319 | 3/1990 | Miyata et al. | 356/136 |
| 4,974,552 | 12/1990 | Sickafus | 356/136 |
| 5,359,681 | 10/1994 | Jorgenson et al. . | |
| 5,477,318 | 12/1995 | Ohsaki et al. | 356/136 |
| 5,565,978 | 10/1996 | Okubo et al. | 356/136 |
| 5,617,201 | 4/1997 | Kåhre | 356/136 |

FOREIGN PATENT DOCUMENTS 0 292 097 A2  11/1988  European Pat. Off. .
0 341 927 A1  11/1989  European Pat. Off. .

OTHER PUBLICATIONS

Melendez, Jose, et al., "A Commercial Solution for Surface Plasmon Sensing", Sixth International Meeting on Chemical Sensors, Gaithersburg, MD, USA, Jul. 22–25 1996; Sensors and Actuators B (Chemical), vol. B35, No. 1–3, ISSN 0925–4005, Elsevier, Switzerland, Sep., 1996, pp. 212–216.

Primary Examiner—Richard A. Rosenberger
Attorney, Agent, or Firm—David Denker; Carlton H. Hoel; Frederick J. Telecky, Jr.

[57] ABSTRACT

Disclosed is an integrated miniaturized biochemical sensor (50) which can be used to make critical angle measurements resulting from the differences in refractive index between the sensor's housing (55) and a given sample (40). In one embodiment, the sensor includes a device platform (111) over which an encapsulating and light transmissive housing (115) is formed to enclose the various sensor components including a light source (105), and a photodetector (107), a signal processing unit (95) and a temperature sensor (95). In another embodiment the housing (115) has a reflective mirrored surface (119) which focuses the light (117) from the light source (105) onto a sensing surface (121) which is in interact with the sample (40) of interest. Light incident from the sensing surface (121) is directed at the photodetector (107,159) which may be an array or single cell. A temperature sensor (95) may also be included and coupled to the platform (111).

27 Claims, 3 Drawing Sheets

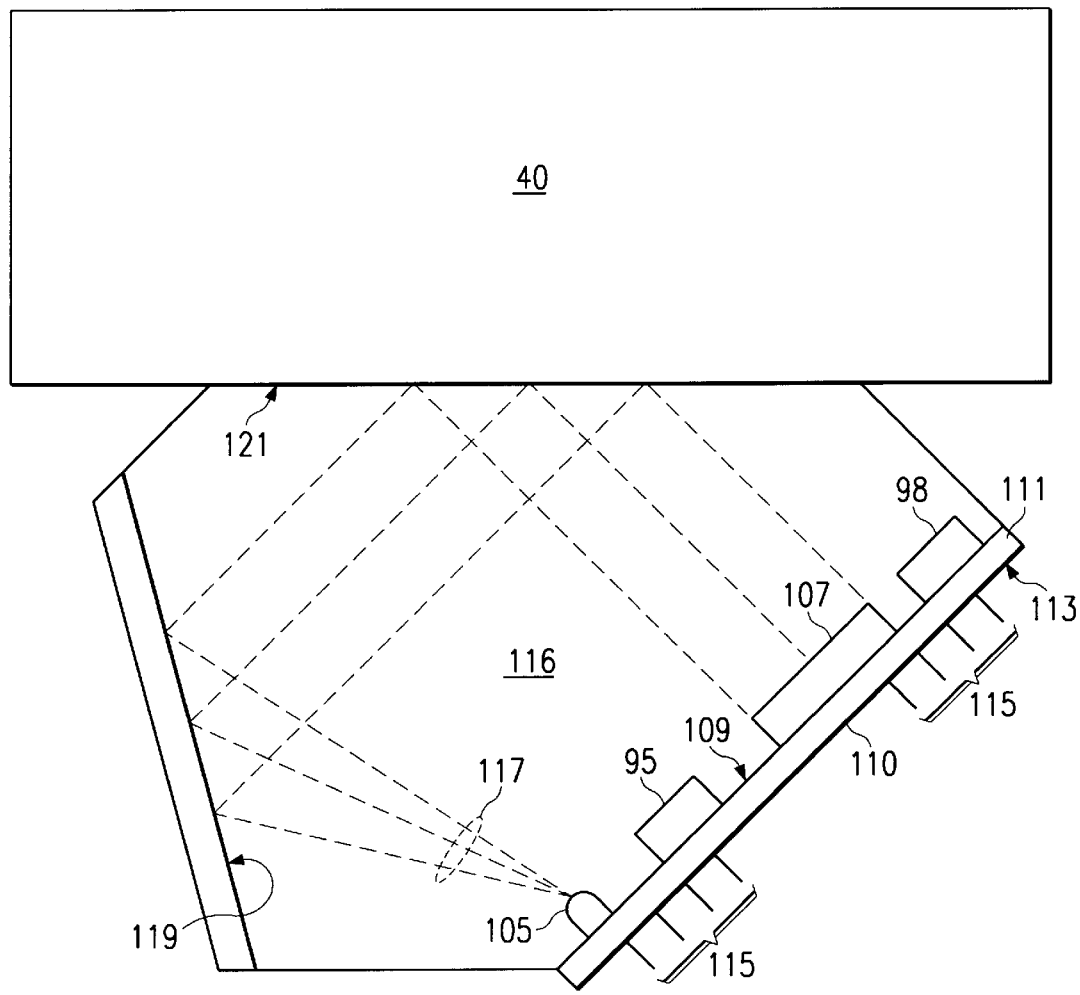

CRITICAL ANGLE SENSOR

TECHNICAL FIELD OF THE INVENTION

The present invention relates in general to the field of optical sensors and in particular to an integrated optical sensing device for making critical angle measurements of light reflected from a surface predisposed about a given sample of interest permitting qualitative or quantitative analysis about the sample.

BACKGROUND OF THE INVENTION

Without limiting the scope of the invention, its background is described in connection with an optical sensor that may be used to detect the presence of a given sample of interest such as a gas, liquid or solid.

Sensing systems for refractive index measurements using critical angle are well known in the art, as are the principles of physics underlying the measurement of critical angle to determine refractive index of a medium. Critical angle is a function of refractive index. At angles of incidence larger than the critical angle, total internal reflection may be observed. Total internal reflection occurs when light rays are incident from a medium of a high index of refraction onto a medium of lower refractive index.

Devices in the prior art typically require a user to interpret the characteristic transition from transmission to total internal reflection; in most refractometers, a liquid is enclosed between two glass prisms and total internal reflection at the interface is observed visually.

Prior current liquid level sensors are sensitive only to the presence or absence of liquid in a given liquid chamber. They also require an optical medium of glass to be in the liquid chamber, which can effect changes in fluid flow patterns.

One embodiment of the present invention provides for detection of not only the presence of a liquid, but whether the liquid is sufficiently composed of a certain constituent. As such, the present invention is particularly useful in compressor operations, in which insufficient oil lubricant causes failure of the compressor. Among the many potential useful applications, the present invention may be used to prevent such failure by determining whether an oil reservoir containing an oil and refrigerant mixture has a sufficient percent composition of oil to keep it from malfunctioning. The present invention may also be employed in quality control applications to detect whether a solution falls below or exceeds a given threshold percentage of a component of interest.

Another limitation of the prior art sensors is that they are large and not fully integrated. The high number of independent components, interface structures, and additional circuitry increases total system cost and maintenance. The present invention solves many of these problems by integrating the electro-optic components within a single protective housing.

A sensing device that integrates the various electro-optical components on a single platform would be advantageous. The device should render data reflecting the critical angle at which total internal reflection is observed. The data should be available in either raw or processed format to permit further analysis by a personal computer or other similar processing system. A device that is small, lightweight and integrated would have widespread application and fill the void left by prior art sensors.

SUMMARY OF THE INVENTION

Most prior art refractometers are of the Abbe type in which total internal reflection is observed visually and, as such, have limited field application. A primary object of the present invention to provide an integrated sensor capable of use in most field applications that provides meaningful critical angle data easily analyzed and interpreted by a computer or other similar system.

Another object of the present invention is to provide a percent composition sensor that detects whether a liquid solution consists of a sufficient fraction of a component of interest. The prior art liquid level sensors are limited in this application in that they detect only presence or absence of a liquid rather than glean data indicative of a sample's percent composition.

Yet another object of the present invention is to provide a low cost sensor that may be manufactured in high volume. The present invention is a miniature, lightweight sensor and uses low-cost components.

Generally, and in one form of the invention, a light source emits electromagnetic radiation at a range of angles within a protective optical housing. One or more mirrored surfaces of the housing direct the light to a sensing surface which is on contact with the sample of interest. Light striking the sensing surface at angles of incidence smaller than the critical angle is partially refracted into the sample and partially reflected within the housing. At angles of incidence greater than the critical angle, light is totally internally reflected towards an onboard photodetector.

The photodetector senses illumination intensity of the reflected light rays. This intensity is at its highest in the total internal reflection region. A transition from high to low is indicative of the critical angle, and can be sensed by the individual cells of the photodetector to produce an output signal. The signal is converted to a corresponding voltage and in one embodiment of the invention, relayed to a signal processing unit.

Once the critical angle is determined, the refractive index of the sample may be determined, which is indicative of one or more sample properties. In another embodiment, a temperature sensor is included to provide temperature monitoring near the sensing surface. All system components are included within the protective optical housing, including the light source, the photodetector, the signal processing circuitry, and the temperature sensor.

An advantage of one embodiment of the present invention is it contains the necessary electro-optic components within a protective encapsulating housing. As such, it accomplishes much of the signal processing itself without requiring additional external circuitry to analyze raw data. Another advantage of the invention is its small size, allowing the device to be employed in a large number of field applications. For example, reference is made to one suitable component for the photodetector, the TSL1401, which has dimensions of approximately 3 in.x0.40"x0.32". In addition to being miniaturized, the sensor components are low-cost and are readily available in the industry. Thus, the sensor may be manufactured in high volumes.

For a more complete understanding of the present invention, including its features and advantages, reference is now made to the following detailed description, taken in conjunction with the accompanying drawings.

BRIEF DESCRIPTION OF THE DRAWINGS

In the drawings:

FIG. 3 depicts an embodiment of a critical angle sensor system in accordance with the present invention.

Corresponding numerals and symbols in the different figures refer to corresponding parts unless otherwise indicated.

DETAILED DESCRIPTION OF THE PREFERRED EMBODIMENT

Figure 1:
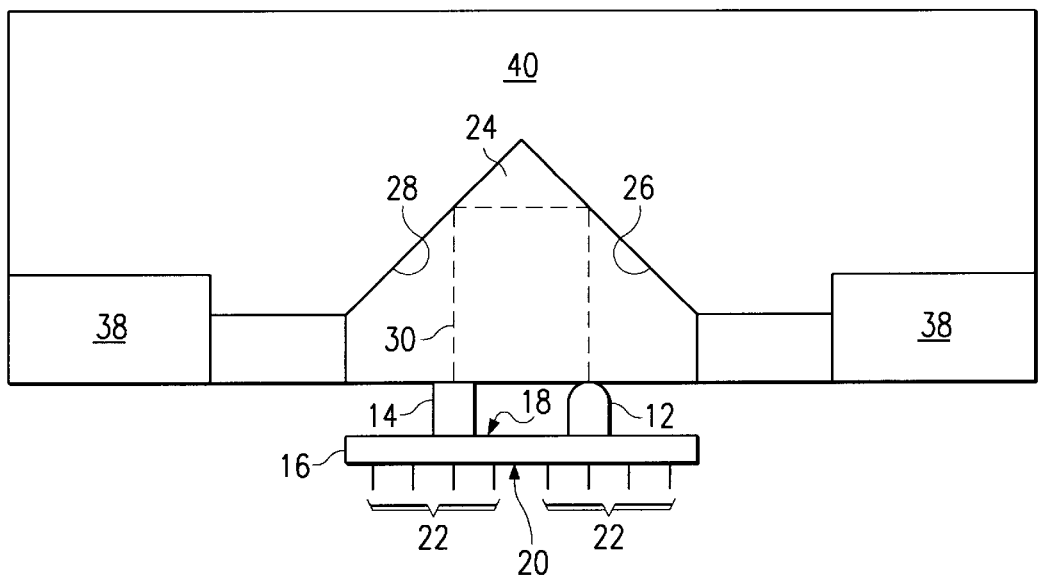
FIG. 1 depicts a prior art liquid level sensor system.

In FIG. 1, a liquid level sensor known to those skilled in the art is shown and denoted generally as 10. The prior art sensor 10 comprises a light source 12 and a photodetector 14, both coupled to an upper surface 18 of the platform 16. A bottom surface 20 of platform 16 has a plurality of conductive pins 22 extending therefrom and provide the interface to the outside world.

Sensor 10 uses a prism-shaped structure 24 predisposed inside a liquid chamber 38 which contains the sample liquid 40. Light 28 emitted from light source 12, reflects off the first prism surface 26 in the direction of a second prism surface 28 where it reflects and is incident on the photodetector 14.

The optical prism 24 is made of a light transmissive material, such as glass or plastic, making the sensor 10 compatible with the environment inside the chamber 38. This configuration, however, poses a problem in that it can cause changes in fluid flow patterns in the sample 40. Furthermore, the sensor 10 is sensitive only to detecting the presence or absence of the liquid sample 40 in the chamber 38.

Figure 2:
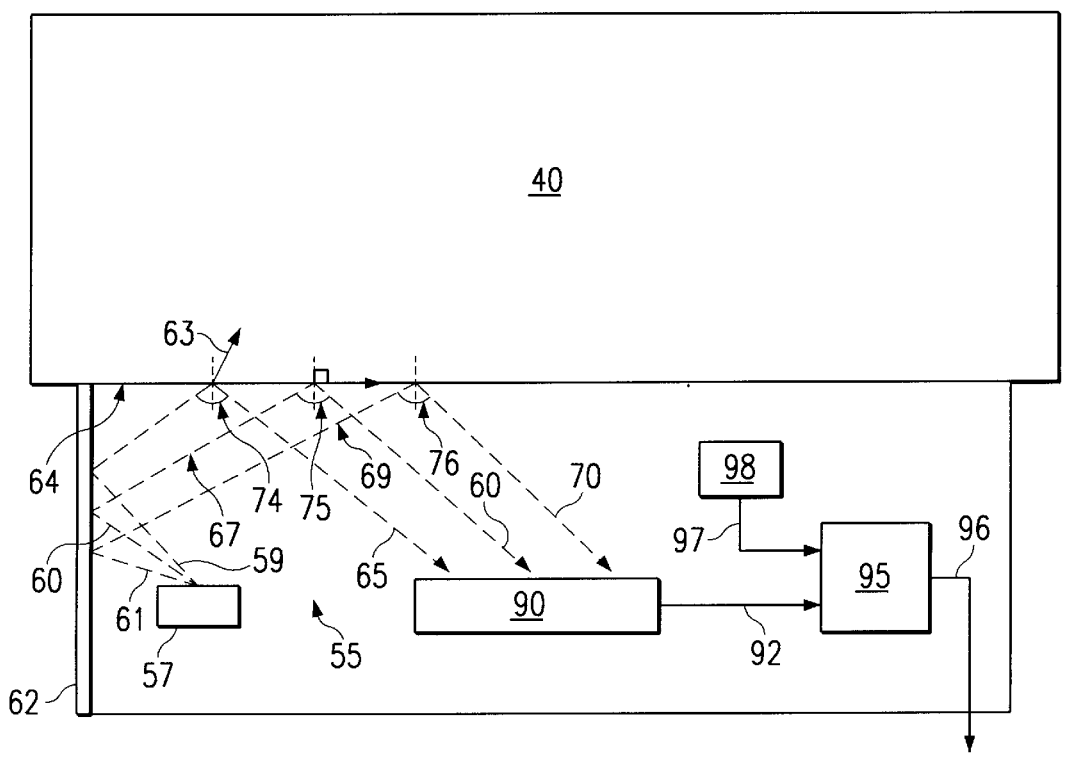
FIG. 2 depicts a general block diagram of an integrated critical angle sensor system.

Turning now to FIG. 2, the advantages of the present invention are made apparent to those skilled in the art, wherein block diagram of an integrated critical angle sensor 50 is shown as 50. Sensor 50 detects the presence of a sample 40 by using critical angle to find the sample's refractive index, as shown in Equation 1 below, where $n_2$ is the index of refraction of the medium of transmission (sample 40), $n_1$ is the index of refraction of the medium of origin (light transmissive housing 55), and $\theta_c$ is the critical angle (75).

$$n_2 = (n_1)(\sin \theta_c). \qquad \text{Eq. 1}$$

As shown in FIG. 2, the necessary electro-optic components are contained within an encapsulating light transmissive housing 55. Light source 57 emits electromagnetic radiation, or light rays, 59, 60, and 61 toward a reflective mirrored surface 62. The light rays 59, 60, and 61 then travel through housing 55 in the direction of sensing surface 64 which forms the interface between the sensor 50 and the sample 40. Thus, the sensing surface 64 is in direct contact with the sample 40.

The plurality of light rays 59, 60 and 61 strike the sensing surface 64 at a range of angles. For angles of incidence smaller than the critical angle 75, a portion of the light is refracted into the sample 40 resulting in an overall loss. This is illustrated by refracted ray 63 which travels into the sample 40 and reflected ray 65 which reflects into housing 55 at angle 74.

At the critical angle 75, a light ray 60 reflects along the sensing surface 64 at 90° angle of refraction minimizing the overall light loss into sample 40.

Thus, a critical angle 75 can be measured as the angle measured between the incident light ray 67 and the normal to the sensing surface 64. For angles of incidence larger than the critical angle 75, such as 76, the incident ray 69 is totally internally reflected within housing 55, with no refracted component, and its full intensity is therefore directed toward photodetector 90. This total internal reflection can only occur when light originates in a medium of a higher index of refraction.

It should be noted, however, that the refractive index of the housing material may be lower than the sample 40. In such a configuration, the sensor 50 can be used to render a threshold level of refractive index eliminating a range less than that of the housing material.

For optical radiation, a suitable photodetector 90 is the TSL213, TSL401, and TSL1401, with a linear array of resolution n×1 consisting of n discrete photo sensing areas, or pixels. Light energy striking a pixel generates electron-hole pairs in the region under the pixel. The field generated by the bias on the pixel causes the electrons to collect in the element while the holes are swept into the substrate. Each sensing area in the photodetector 90 thereby produces a signal on an output with a voltage that is proportional to the intensity of the radiation (60, 65, 70) striking the photodetector 90. This intensity and its corresponding voltage are at their maxima in the total internal reflection region.

It should be understood that various means of photodetection are contemplated by the invention including an n×1 cell photodetector such as the TSL213, TSL401, and TSL1401. In addition, a single cell photo resistor, bolometer, positive sensitive detector, pyroelectric device as well as other devices may be used.

As described, a range of angles of the reflected light rays are projected onto photodetector 90. The critical angle is marked by a transition from high to low. The output, representing bit level data from the photodetector 90, is transmitted within housing 55 via interface 92 to a signal processing unit 95 for further qualitative and/or quantitative analysis.

The signal processing unit 95 may provide the necessary interface control signals, such as clock line and serial input, for protocol communications with the photodetector 90. Signal processing unit 95 may be used increasing the sensor's over that obtained by the photodetector 90 pixel resolution. It should be understood, however, that the signal processing unit 95 is disclosed in conjunction with a contemplated embodiment and, as such, does not constitute a necessary component of the invention.

When used, signal processing unit 95 is preprogrammed to analyze and characterize the intensity, occurrence and timing of light rays 60, 65, and 70 to obtain qualitative and quantitative information about the sample 40. For example, signal processing unit 95 can be preprogrammed to determine the total amount of time that sample 40 is within a given proximity of the sensor 50. Also, signal processing unit 95 can be preprogrammed to determine the frequency of sample 40 over a given period of time. As can be appreciated, other results are also possible and within the scope of the present invention.

Output data from signal processing unit 95 may be transmitted via interface 96 to a secondary system, such as a computer, hand-held meter, calculator, printer, logic analyzer, or other similar system (not shown). In various embodiments, the interface 96 comprises a plurality of conductive pins, giving the sensor a platform similar to an integrated circuit package.

Sensor 50 may also include a temperature sensor 98 within the housing 55. Temperature sensor 98 produces an electrical signal indicative of the temperature of the sensor surface 64 during operation thereof. This temperature signal may be relayed to signal processing unit 90 via interface 97. Temperature data can be utilized to compensate for apparent changes in the measured index of refraction as a result of changes in the operating temperature.

In reference to FIG. 3, a specific embodiment of sensor 50 in accordance with the present invention is shown and denoted as 100. The electro-optic components of sensor 100, including light emitting diode 105, photodetector array 107, signal processing unit 95, and temperature sensor 98, are all encapsulated within the trapezoidal-shaped housing 115 and coupled to an upper surface 109 of a platform 111. A plurality of conductive leads 115 are operably coupled to a bottom surface 113 of platform 111.

Housing 115 has an optical geometry such that light 117 from LED 105 will reflect from mirrored surface 119 to sensing surface 121 and then strike photodetector 107. It is desirable to have the radiation strike the photodetector 107 at angles as close as possible to 90°. By shaping sensor 100 such that light 117 strikes the photodetector 107 at an angle close to 90°, the photodetector 107 will have the maximum possible sensitivity. It should be understood, however, that other configurations of housing 115 may be employed consistent with the present invention.

Also, sensing surface 121 is depicted as planar in FIG. 3, but other geometries may be employed. Specifically, sensing surface 121 may have a convex, concave shaped or may be otherwise fitted.

Housing 115 is made of a light transmissive material in which light 117 from light source 105 travels. Suitable materials include glass, plastic or hardened epoxy, although other materials may be used that preferably will not damage the encapsulated components. In particular, an epoxy marketed under the trademark Epocast® 2013 Parts A/B by Furane Products Company has been found useful, especially for radiation sources in the infrared range. Other usable materials include Emerson & Cumming, Stycast 1269A Parts A/B, Tracon Trabond F114, Dexter Hysol OS1000, Norland 61 and 63, Dexter Hysol MG18, and Nitto 8510-1100.

Housing 115 is coupled to the platform 111 to form an encapsulated self-contained sensor. In one embodiment of the invention, platform 111 is made of a dark, light-absorbing material, such as a hard resin or epoxy. However, the material of platform 111 depends primarily on the radiation properties of light source 105. Also, platform 111 could be coated with a dark layer of light-absorbing material such as polyurethane epoxy or a thin resin layer among others.

As shown, embedded within housing 115 and operably coupled to a surface 109 of platform 111 is light source 105. Light source 105 may comprise a light emitting diode (LED), laser diode, light filament, halogen lamp, or other suitable source of electromagnetic radiation. Also, in one embodiment of the invention, a plurality of light sources that emit light of different wavelengths are used.

The mirrored surface 119 of housing 115 is disposed adjacent light source 105 such that light rays 117 travel from light source 105, strike surface 119, and reflect toward sensing surface 121. The sensing surface 121 may be planar, convex, concave or otherwise fitted. In another embodiment (not shown) of the invention, surface 119 is disposed near the photodetector 107 such that light rays 117 from light source 105 reflect off the sensing surface 121 toward surface 119 and then off surface 119 towards photodetector 107.

Surface 119 is depicted as a planar surface of sensor 100, although, surface may be concave or convex, consistent with the present invention. Also, in another embodiment of the invention, a plurality of mirrored surfaces are utilized to direct light rays 117 from light source 105, to sensing surface 121, and ultimately to photodetector 107.

The photodetector 107 is embedded within housing 115 and operably coupled to platform 111. Suitable photodetectors 107 include without limitation the TSL213, TSL401, and TSL1401. Likewise, signal processing unit 95 is embedded within housing 105 and coupled to platform 111 and operably interfaced to photodetector 95 via well known methods.

Temperature sensor 98 is also embedded within housing 105 and coupled to upper surface 109 of platform 111. It is desirable that temperature sensor 98 be disposed as close to the sensing surface 121 as is practical.

A filter may be used to screen out radiation at wavelengths other than wavelengths produced by light source 105. This filter (not shown) would overly photodetector 107 and serves to pass radiation at the wavelengths produced by light source 105 to photodetector 107. As such, the filter eliminates unwanted noise caused by other radiation sources in proximity to the sensor 100. One suitable filter is the plastic filter material marketed by Polaroid Corporation and known as XR-84. This material is especially suitable for passing infrared radiation and blocking visible radiation.

An alternative to utilizing a filter is to utilize a plastic or epoxy material for the housing 105 which is transparent to wavelengths produced by the light source 105 and opaque to frequencies outside the desired frequency range of interest for a given sensor/sample combination. Likewise, an absorbing die can be enclosed in the housing 105 to achieve the same function.

Those of skill in the art will recognize that the elements of sensor 100 can be relocated, rearranged or about the sensor platform 111 while retaining equivalence in function according to the invention. For example, mirrored surfaces 119 utilized for reflecting the light rays 117 could take on other configurations and locations within the sensor 100 so long as the light 117 strikes the sensing surface 121 and the intensity of the radiation reflected therefrom is measured as a function of the angle of the radiation striking the sensing surface 121.

Figure 4A:
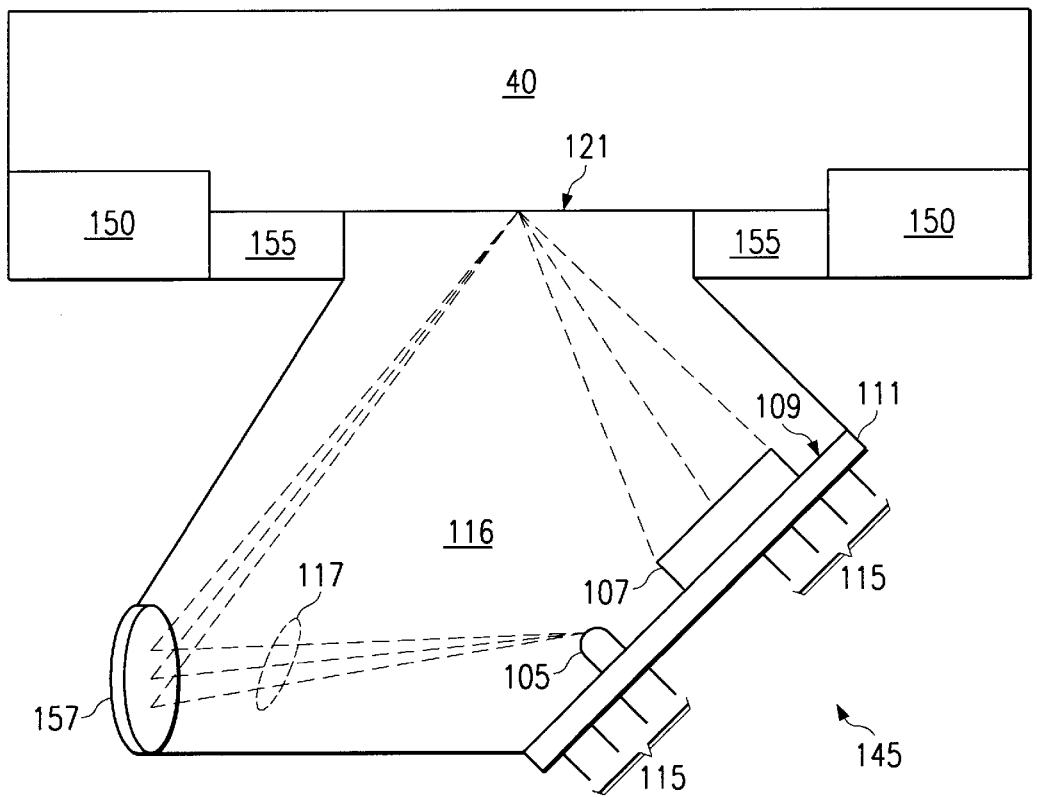
FIG. 4a illustrates an alternative embodiment of a sensor for deriving critical angle measurements over a range of angles.
Figure 4B:
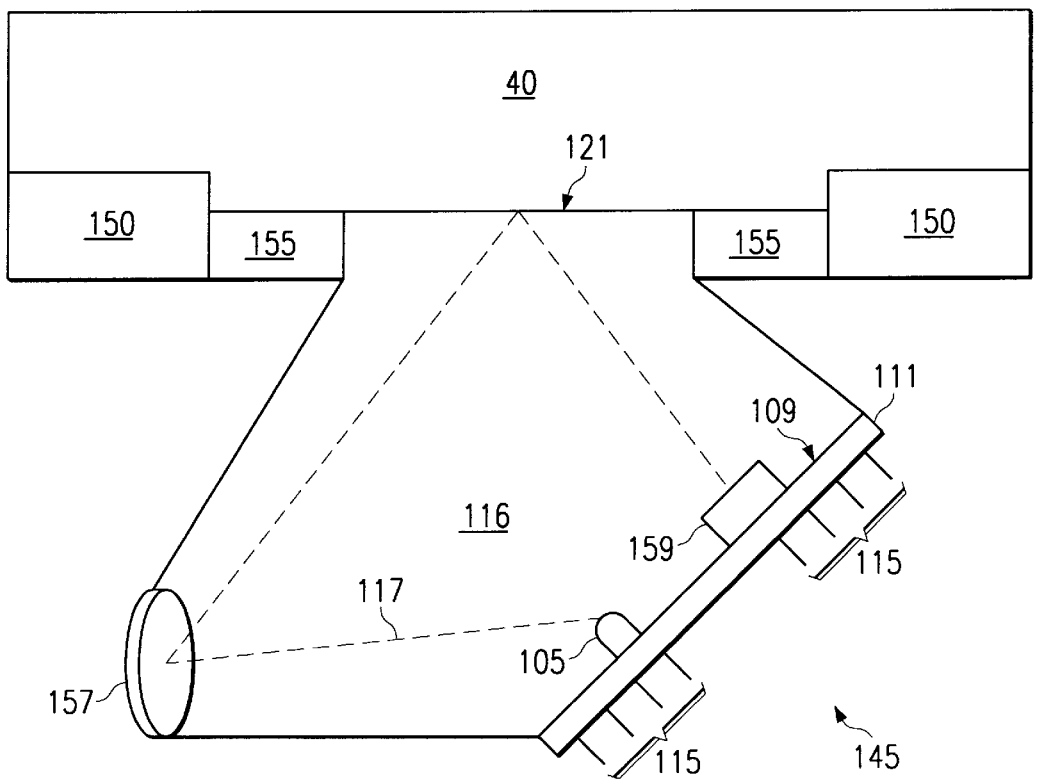
FIG. 4b illustrates an alternative embodiment of a sensor for deriving critical angle measurements from a single ray of incident light.

Further alternative embodiments of a critical angle sensor system consistent with the present invention are illustrated in FIGS. 4a and 4b. In FIG. 4a, the housing 1150 is secured to a sample container 150 using sealant 155 near the sensing surface 121. As shown, light 117 radiates from light source 105 at a range of angles in the direction of curved mirrored surface 157. Light 117 is focused and reflected off surface 157 toward sensing surface 121. Light 117 is then reflected from sensing surface 121 towards a photodetector 107 which comprises an n×1 photodetector array with n cells of the type well known in the art.

Photodetector array 107 receives the light incident over a broad range of angles and yields a binary output of either high or low for each light cell where sufficient light is sensed. The output of each cell can be carried on interface 115, as individual binary signals of each photo cell, to an external system (not shown), such as a computer, hand-held meter, calculator, printer, logic analyzer, oscilloscope, or other similar system. Thus, the present invention makes use of the variation of critical angle with refractive index along sensing surface 121.

Yet another embodiment of a critical angle sensor system according to the invention is shown in FIG. 4b wherein the light 117 from light source 105 comprises a single ray of light directed at surface 157 and in the direction of sensing surface 121. Light incident the sensing surface 121 is directed at the photodetector 159 which in this case comprises a single cell photodetector which has been prepositioned at a predetermined location on platform 111.

The photodetector 159 is of the type well known in the art and its location on platform 111 corresponds to a specific angle of refractive index. Thus, in FIG. 4b the sensor 145 is configured to detect light incident at a given critical angle corresponding to the location of the photodetector 154 about the upper surface 109 of platform 111. The output from the detector cell 159 is a single bit present/no present indicator that appears at interface 115 and can be transferred to a remote processing system for further qualitative and/or quantitative analysis.

While this invention has been described with reference to illustrative embodiments, this description is not intended to be construed in a limiting sense. Various modifications and combinations of the illustrative embodiments as well as other embodiments of the invention will be apparent to persons skilled in the art upon reference to the description. It is, therefore, intended that the appended claims encompass any such modifications or embodiments.

What is claimed is:

1. An integrated critical angle sensor comprising:
   platform having an upper surface and a bottom surface;
   a unitary light transmissive housing coupled to said platform and having an outer sensing surface, the housing made of a single piece of material;
   a photodetector array coupled to said upper surface of said platform and integrally encapsulated in said light transmissive housing; and
   a light source coupled to said upper surface of said platform adjacent said photodetector array, said light source integrally encapsulated in said light transmissive housing and spatially arranged inside said light transmissive housing to emit light in the direction of said sensing surface, a portion of said light being internally reflected off the interface between said sensor and a sample of interest in the direction of said photodetector array, said photodetector array calibrated to determine the relative intensity of light emitted and light reflected.

2. The system as recited in claim 1 wherein said housing is composed of a material having a higher index of refraction than the sample of interest.

3. The system as recited in claim 1 wherein said housing is composed of light transmissive epoxy material.

4. The system as recited in claim 1 wherein said housing has a substantially pyramidal shape.

5. The system as recited in claim 1 wherein said housing has a substantially trapezoidal shape.

6. The system as recited in claim 1 wherein said photodetector array is a linear solid state photoarray.

7. The system as recited in claim 1 further comprising a light reflective surface spatially inside said housing to receive light from said light source and direct it towards said photodetector array.

8. The system as recited in claim 7 wherein said reflective surface is a planar surface.

9. The system as recited in claim 7 wherein said reflective surface is a concave surface.

10. The system as recited in claim 1 further comprising a plurality of other light sources coupled to said upper surface of said platform and configured to emit light rays of different wavelengths.

11. The system as recited in claim 1 further comprising a signal processing unit coupled to said upper surface of said platform and electronically connected to said photodetector array.

12. The system as recited in claim 11 wherein the signal processing unit is preprogrammable.

13. The system as recited in claim 1 further comprising a plurality of conductive leads coupled to said bottom surface of said platform and forming conductive pathways to said photodetector array.

14. The system as recited in claim 1 further comprising a temperature sensor embedded in said housing.

15. The system as recited in claim 14 wherein said temperature sensor is disposed in close proximity to said sensing surface of said housing.

16. The system as recited in claim 1 wherein said housing is composed of a material having a lower index of refraction than the sample of interest.

17. An optical critical angle sensor for measuring the positional intensity of incident light reflected from an interface between the sensor and a sample of interest, the sensor comprising:
   a platform having an upper surface and a bottom surface;
   a first light source coupled to said upper surface of said platform;
   a photodetector array coupled to said upper surface of said platform adjacent said first light source;
   a unitary housing extending over said first surface to integrally encapsulate said light source and said photodetector array, said housing having a sensing surface which forms the interface between said sensor and said sample of interest, said housing also having a first surface, the first surface forming a front face of a reflective mirror, the mirror spatially arranged to receive light from said light source and direct it towards said sensing surface, said housing made of a single piece of material with a refractive index selected for its known relation to the refractive index of said sample.

18. The sensor as recited in claim 17 wherein said photodetector array is a linear array.

19. The sensor as recited in claim 17 wherein said housing has an optical geometry that allows light from said light source to strike said sensing surface and reflect off said sensing surface to strike said photodetector array.

20. The system as recited in claim 17 wherein said housing is composed of a medium with a higher index of refraction as compared to the sample of interest.

21. The system as recited in claim 17 wherein said first surface is a planar surface.

22. The system as recited in claim 17 wherein said first surface is a concave surface.

23. A critical angle sensor comprising:
   a device platform having an upper surface with at least one light emitting diode and a photodetector array coupled thereto and a bottom surface with a plurality of signal pins extending therefrom; and a unitary light transmissive optical housing made from a single piece of material coupled to said platform in an encapsulating manner over said upper surface, said housing integrally encapsulating said light emitting diode and said photodetector array, said housing having a first surface and a sensing surface, said first surface forming the front face of a reflective mirror, the reflective mirror predisposed to receive light from said light source and direct it towards said sensing surface and said sensing surface predisposed to direct light towards said photodetector array.

24. The sensor as recited in claim 23 further comprising a signal processing unit coupled to said upper surface of said platform and electronically interconnected between said photodetector array and said plurality of signal pins.

25. The system as recited in claim 24 wherein the signal processing unit is preprogrammable.

26. The sensor as recited in claim 23 wherein said photodetector array is a linear solid state photoarray.

27. The system as recited in claim 23 further comprising a temperature sensor coupled to said upper surface of said platform and embedded in said housing.

* * * * *

UNITED STATES PATENT AND TRADEMARK OFFICE
CERTIFICATE OF CORRECTION

PATENT NO.    : 6,097,479
DATED         : August 1, 2000
INVENTOR(S)   : Jose L. Melendez, Richard A. Carr and Dwight U. Bartholomew It is certified that error appears in the above-identified patent and that said Letters Patent is hereby corrected as shown below:

Cover Page, Item [60], Continuing Data:
add --Provisional application No. 60/027,286, Oct. 01, 1996.--

Column 1, between lines 1 and 2:
add --This application claims priority under 35 U.S.C. § 119(e)(1) of provisional application number 60/027,286 filed 10/01/96.--

Signed and Sealed this

Twelfth Day of June, 2001

*Attest:*

NICHOLAS P. GODICI
*Attesting Officer*   *Acting Director of the United States Patent and Trademark Office*